United States Patent [19]

Hunt et al.

[11] Patent Number: 4,790,870

[45] Date of Patent: Dec. 13, 1988

[54] HERBICIDALLY ACTIVE ARYLOXY OPTIONALLY OXO-SUBSTITUTED INDANE OR TETRALIN DERIVATIVES

[75] Inventors: David A. Hunt, Copley; James A. Schwindeman, Akron, both of Ohio

[73] Assignee: PPG Industries, Inc., Pittsburgh, Pa.

[21] Appl. No.: 44,675

[22] Filed: May 1, 1987

[51] Int. Cl.$^4$ ............................................. A01N 43/40
[52] U.S. Cl. .......................................... 71/94; 71/121; 71/122; 71/123; 546/302; 546/300; 564/265; 568/328; 568/633
[58] Field of Search ................... 71/105, 94, 121, 122, 71/123; 568/327, 328, 633; 546/300, 302; 564/265

[56] References Cited

U.S. PATENT DOCUMENTS

| | | | |
|---|---|---|---|
| 4,291,050 | 9/1981 | Waltersdorf et al. | 568/327 |
| 4,333,949 | 6/1982 | Sturm et al. | 568/327 |
| 4,419,122 | 12/1983 | Swithenbank | 71/105 |

OTHER PUBLICATIONS

Wheeler, Chem. Abst., vol. 101, #90609m (1984).
Haddock et al., Chem. Abst., vol. 104, #50785w (1986).
Rufer et al., Chem. Abst., vol. 97, #55433b (1982).
Nielson, Chem. Abst., vol. 106, #18,536w (1987).

*Primary Examiner*—James H. Reamer
*Attorney, Agent, or Firm*—Alice C. Brennan

[57] ABSTRACT

This invention relates to aryloxy optionally oxo-substituted indane or tetralin derivatives having herbicidal activity and to the use of such compounds to control the growth of noxious plants, i.e., weeds.

3 Claims, No Drawings

HERBICIDALLY ACTIVE ARYLOXY OPTIONALLY OXO-SUBSTITUTED INDANE OR TETRALIN DERIVATIVES

FIELD OF THE INVENTION

This invention relates to aryloxy optionally oxo-substituted indane or tetralin derivatives having herbicidal activity and to the use of such compounds to control the growth of noxious plants, i.e., weeds.

DESCRIPTION OF THE INVENTION

This invention provides herbicidally active aryloxy optionally oxo-substituted indane or tetralin compounds represented by the Formula I:

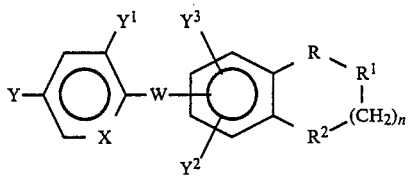

wherein:
W is O or $S(O)_x$ wherein x is 0, 1 or 2;
X is N or $CY^4$ wherein $Y^4$ is hydrogen, halogen, cyano, nitro or $C_1$ to $C_4$ haloalkyl;
Y, $Y^1$, $Y^2$ and $Y^3$ are independently hydrogen, halogen, cyano, nitro or $C_1$ to $C_4$ haloalkyl;
R and $R^1$ are independently $CZZ^I$ wherein Z is hydrogen or halogen; and $Z^1$ is hydrogen, halogen, cyano, hydroxy or $C_1$ to $C_4$ alkyl or alkoxy; or CO or $CS(O)_x$ wherein x is 0, 1 or 2; or $CNOR^3$ wherein $R^3$ is hydrogen, $C_1$ to $C_4$ alkyl, up to $C_4$ alkenyl or alkynyl, carboxy or up to $C_{10}$ carboalkoxyalkyl; or $OCOR^6$, $S(O)CO_xR^6$ or $COR^6$ wherein $R^6$ is hydrogen, $C_1$ to $C_4$ alkyl or haloalkyl, $OR^7$, $SR^7$ or $NR^8R^9$ wherein $R^7$ is hydrogen, halogen, alkali metal, ammonium, up to $C_6$ alkyl, haloalkyl, oxoalkyl, hydroxyalkyl, thioalkyl, alkoxyalkyl, cycloalkyl, alkenyl, alkynyl or up to $C_{10}$ alkoxycarbonyl alkyl including amides or salts thereof, or phenyl or benzyl; $R^8$ and $R^9$ are independently hydrogen, or up to $C_6$ alkyl, alkoxy, alkoxyalkyl, alkenyl or alkynyl;
$R^2$ is $CH_2$, CO or $CS(O)_x$ wherein x is 0, 1 or 2; and n is 0 or 1.

Preferred compounds of the Formula I are those wherein Y is trifluoromethyl, $Y^1$ is halogen, especially chlorine or fluorine; X is N or $CY^4$ wherein $Y^4$ is halogen, especially chlorine or fluorine; W is oxygen, $R^1$ and $R^2$ are each $CH_2$; n is 1; and R is CO, CHOH or CNOH.

The compounds of this invention may be readily synthesized using methods known to the art. For example, a suitably substituted benzene or pyridine of the Formula II:

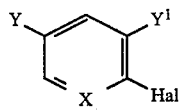

wherein Y, $Y^1$ and X are as previously defined and Hal is halogen, preferably chlorine, bromine or fluorine, is reacted with a suitably substituted indanone or tetralone derivative of the formula III:

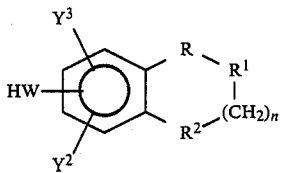

wherein W, $Y^2$, $Y^3$, R, $R^1$, $R^2$ and n are as previously defined to form a compound of the Formula I. Alternatively, certain of the Formula I compounds may be used as intermediates to prepare other compounds within the scope of Formula I. For example, a tetralone (or indanone) prepared by reacting a suitably substituted Formula II and Formula III compound and having the Formula IV:

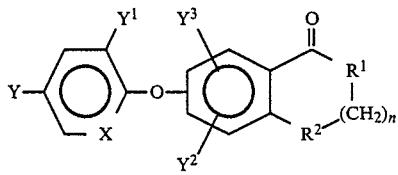

may be reacted with a suitably substituted amine of the Formula V:

wherein $R^3$ is as previously defined, to form the corresponding tetralone oxime.

The following Examples are illustrative of the preparation of certain compounds of the invention.

EXAMPLE I

Preparation of:
6-(2-chloro-6-fluoro-4-trifluoromethylphenoxy)-tetralone

A stirred mixture containing 2.64 grams (0.0122 mole) of 2-chloro-3,4-difluorobenzotrifluoride, 2.00 grams (0.0122 mole) of 6-hydroxytetralone, 2.02 grams (0.01464 mole) of potassium carbonate and 125 milliliters of acetonitrile was refluxed, under a calcium chloride drying tube, for about 18 hours. The reaction mixture was then cooled, diluted with 200 milliliters of water and extracted with 2×125 milliliter portions of chloroform. The organic extracts were dried over anhydrous magnesium sulfate, filtered and concentrated in vacuuo affording 3.87 grams of tan solid confirmed by spectroscopic analysis as the desired product.

EXAMPLE II

Preparation of:
6-(2-chloro-6-fluoro-4-trifluoromethylphenoxy)-tetralol

A solution of 1.15 grams (0.00319 mole) of the tetralone, prepared as described in Example I, in 30 milliliters of ethanol was added dropwise, under a nitrogen blanket, to a stirred mixture of 0.197 gram (0.00521 mole) of sodium borohydride in 30 milliliters of ethanol. After stirring, under a nitrogen blanket at room temperature, for about 18 hours excess borohydride was quenched by addition of acetic acid and the resulting clear solution was diluted with water and extracted with 2×10 milliliter portions of methylene chloride. The organic extracts were dried over anhydrous magnesium sulfate, filtered and concentrated in vacuuo affording 1.16 grams of a pale yellow syrup confirmed by spectroscopic analysis as the desired product.

EXAMPLE III

Preparation of: 6-(2-chloro-6-fluoro-4-trifluoromethylphenoxy)-tetralone oxime

A stirred mixture of 2.00 grams (0.00555 mole) of the tetralone, prepared as described in Example I, 0.46 gram (0.00661 mole) of hydroxylamine hydrochloride, 0.99 gram (0.00727 mole) of sodium acetate trihydrate, 30 milliliters of ethanol and 10 milliliters of water was warmed on a steam bath until solution was complete. After stirring at room temperature for about four days, the reaction mixture was concentrated in vacuuo, the residue was taken up in water and extracted with 2×125 milliliter portions of chloroform. The organic extracts were dried over anhydrous magnesium sulfate, filtered and concentrated in vacuuo affording 2.08 grams of white solid confirmed by spectral analysis as the desired product.

EXAMPLE IV

Preparation of: 6-(2-chloro-6-fluoro-4-trifluoromethylphenoxy)-tetralone oxime-O-(alpha-methyl methyl-acetoxyl)ether A stirred mixture of 0.54 gram (0.00144 mole) of the tetralone oxime, prepared as described in Example III, 0.24 gram (0.00144 mole) of 2-bromopropionic acid methyl ester, 0.238 gram of potassium carbonate and 50 milliliters of acetonitrile was refluxed under a calcium chloride drying tube for about 18 hours. The reaction mixture was then cooled, diluted with water and extracted with 2×75 milliliter portions of methylene chloride. The organic extracts were dried over anhydrous, magnesium sulfate, filtered and concentrated in vacuuo affording 0.60 gram of yellow syrup confirmed by spectroscopic analysis as the desired product.

EXAMPLE V

Following the procedure described in Example IV, the compound 6-(2-chloro-6-fluoro-4-trifluoromethylphenoxy)-tetralone oxime-O(methylacetoxyl)ether was prepared by reacting the tetralone oxime prepared as described in Example III with methylbromoacetate.

EXAMPLE VI

Following the procedure described in Example I, the compound 7-(2-chloro-6-fluoro-4-trifluoromethylphenoxy)-alpha-tetralone was prepared by reacting 3-chloro-4,5-difluoro-benzotrifluoride with 7-hydroxy tetralone.

EXAMPLE VII

Following the procedure described in Example II, the compound 7-(2-chloro-6-fluoro-4-trifluoromethylphenoxy)-alpha-tetralone was prepared by reacting the tetralone prepared as described in Example VI with ethanol in the presence of sodium borohydride.

EXAMPLE VIII

Following the procedure described in Example III the compound 7-(2-chloro-6-fluoro-4-trifluoromethylphenoxy)-alpha-tetralone oxime was prepared by reacting the alpha tetralone prepared as described in Example VI with hydroxylamine hydrochloride in the presence of sodium acetate trihydrate and ethanol.

EXAMPLE IX

Preparation of: 6-(2-chloro-4-trifluoromethylphenoxy)tetralone

A stirred mixture of 0.993 gram (0.005 mole) of 3-chloro-4-fluoro-benzotrifluoride, 0.81 gram (0.005 mole) of 6-hydroxytetralone, 1.17 gram (0.0085 mole) of potassium carbonate and 125 milliliters of acetonitrile was refluxed, under a calcium chloride drying tube for about 116 hours. The reaction mixture was then cooled, diluted with 250 milliliters of water and extracted with 250 milliliters of methylene chloride. The organic extracted was dried over anhydrous magnesium sulfate, filtered and concentrated in vacuuo affording 0.75 gram of pale brown syrup confirmed by spectroscopic analysis as the desired product.

EXAMPLE X

Preparation of: 7-(5-trifluoromethyl-2-pyridyloxy)-alphatetralone

A stirred mixture of 1.82 grams (0.010 mole) of 2-chloro-5-trifluoromethyl pyridine, 1.64 grams (0.010 mole) of 7-hydroxytetralone, 2.41 grams (0.0175 mole) of potassium carbonate and 125 milliliters of acetonitrile was refluxed, under a calcium chloride drying tube for about 90 hours. The reaction mixture was cooled, diluted with 200 milliliters of water and extracted with 2.·.200 milliliter portions of methylene chloride. The organic extracts were dried over anhydrous magnesium sulfate, filtered and concentrated in vacuuo affording a brown solid, which upon recrystallization from hexane, afforded 2.62 grams of tan granular solid confirmed by spectroscopic analysis as the desired product.

EXAMPLE XI

Preparation of 7-(5-trifluoromethyl-2-pyridyloxy)-alphatetralol

A solution of 0.90 gram (0.00291 mole) of the alpha-tetralone, prepared as described in Example X) in 35 milliliters of ethanol was added dropwise, under a nitrogen blanket, to a stirred mixture of 0.18 gram (0.00476 mole) of sodium borohydride in 25 milliliters of ethanol. The resulting pink solution was stirred overnight at room temperature under a nitrogen blanket after which excess sodium borohydride was quenched by dropwise addition of acetic acid until gas evolution was complete. The reaction mixture was then concentrated in vacuuo affording 0.86 gram of white, waxy solid confirmed by spectroscopic analysis as the desired product.

EXAMPLE XII

Preparation of 7-(5-trifluoromethyl-2-pyridyloxy)-alphatetralone oxime

A stirred mixture of 0.96 gram (0.00311 mole) of the alphatetralone, prepared as described in Example X, 25 milliliters of water, 0.26 gram (0.0037 mole) of hydroxyl amine hydrochloride, 0.55 gram (0.00407 mole) of sodium acetate trihydrate and 45 milliliters of ethanol was warmed on a steam bath until solution was complete. The reaction mixture was then concentrated in vacuuo and the residue was portioned between methylene chloride and water. The organic portion was dried over anhydrous magnesium sulfate, filtered and concentrated in vacuuo affording 0.98 gram of a pale yellow syrup confirmed by spectroscopic analysis as the desired product.

EXAMPLE XIII

Following the procedure described in Example X the compound 6-(5-trifluoromethyl-2-pyridyloxy)-tetralone was prepared by reacting 6-hydroxytetralone with 2-chloro-5-trifluoromethyl pyridine.

EXAMPLE XIV

Preparation of:
5-(2-chloro-6-fluoro-4-trifluoromethylphenoxy)indane

A stirred mixture of 3.46 grams (0.016 mole) of 2-chloro-3,4-difluoro benzotrifluoride, 2.15 grams (0.016 mole) of 5-hydroxyindane, 3.15 grams (0.0228 mole) of potassium carbonate and acetonitrile was refluxed for about 18 hours. The reaction mixture was then diluted with 120 milliliters of pH 7.0 buffer solution (all suspended solids dissolved). The resulting aqueous solution (pH=10.5) was extracted with 4×400 milliliter portions of chloroform. The organic extracts were then dried over anhydrous magnesium sulfate, filtered and concentrated in vacuuo affording 5.32 grams of a golden oil confirmed by spectroscopic analysis as the desired product.

EXAMPLES XV through XX

Following the procedures described in the foregoing Examples I through XIV as well as other preparative techniques known to the art, the following compounds were prepared:

XV The compound: 5-(2-chloro-6-fluoro-4-trifluoromethylphenoxy)-1-indanone.

XVI The compound: 5-(2-chloro-6-fluoro-4-trifluoromethylphenoxy)-1-indanol.

XVII The compound: 2-formyl-6-(2-chloro-6-fluoro-4-trifluoromethylphenoxy)tetralone.

XVIII The compound: 7-(3-chloro-5-trifluoromethyl-2-pyridyloxy)tetralone.

XIX The compound: 2,2-dibromo-6-(2-chloro-6-fluoro-4-trifluoromethylphenoxy)tetralone.

XX The compound: 2-bromo-6-(2-chloro-6-fluoro-4-trifluoromethylphenoxy)tetralone.

XXI The compound: 5,6,7,8-tetrahydro-2-(2-chloro-6-fluoro-4-trifluoromethylphenoxy)-naphthalene.

The compounds prepared according to the foregoing Examples I to XXI are represented by the following generally Formula VI:

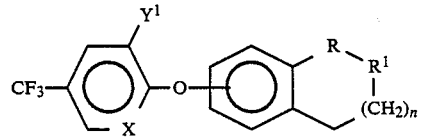

VI.

wherein X, $Y^1$, n, $R^1$ and R are as follows:

| Example | X | Y | n | $R^1$ | R |
|---|---|---|---|---|---|
| I | CCl | F | 1 | CH$_2$ | CO |
| II | " | " | " | " | CHOH |
| III | " | " | " | " | CNOH |
| IV | " | " | " | " | CNOCH(CH$_3$)COOCH$_3$ |
| V | " | " | " | " | CNOCH$_2$COOCH$_3$ |
| VI | " | " | " | " | CO |
| VII | " | " | " | " | CHOH |
| VIII | " | " | " | " | CNOH |
| IX | " | H | " | " | CO |
| X | N | " | " | " | CO |
| XI | " | " | " | " | CHOH |
| XII | " | " | " | " | CNOH |
| XIII | " | " | " | " | CO |
| XIV | " | " | 0 | " | CH$_2$ |
| XV | CCl | F | " | " | CO |
| XVI | " | " | " | " | CHOH |
| XVII | " | " | 1 | CO | CO |
| XVIII | N | Cl | " | CH$_2$ | CO |
| XIX | CCl | F | 1 | CBr$_2$ | CO |
| XX | " | " | " | CHBr | CO |
| XXI | " | " | " | CH$_2$ | CH$_2$ |

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is affected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound or acre of a compound of this invention would be expected to provide satisfactory weed control, although in some instances application rates in excess of one pound per acre, e.g., up to 2 or more pounds per acre might be required. Of course, the efficacy of a particular compound against a particular weed species may readily be determined by routine laboratory or field testing in a manner well known to the art. The compounds of the invention have exhibited herbicidal activity at an application rate as low as 0.025 pound per acre. It is expected that in most instances satisfactory weed control can be had at postemergence application rates in the range of 0.05 to 0.5 pound per acre and at preemergence application rates in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When desired, a compound of this invention can be applied in combination with other herbicidal agents *in an agent in an effort* to achieve even broader vegetative control. Typical herbicides, which can be conveniently combined with Formula I compound, include atrazine, haxazinone, metribuzin, ametryn, cyanazine, cyprazine, prometon, prometryn, propazine, simazine, terbutryn, propham, alachlor, acifluorfen, bentazon, metalachlor and N,N-dialkyl thiocarbamates such as EPTC, butylate or venolate. These, as well as other herbicides described, for example, in the *Herbicide Handbook of the Weed Science Society of America,* may be used in combination with a compound or compounds of the invention. Typically such formulations will contain from about 5 to about 95 percent by weight of a compound of this invention.

The herbicidal formulations contemplated herein can be applied by any of several methods known to the art. Generally, the formulation will be surfaced applied as an aqueous spray. Such application can be carried about by conventional ground equipment, or if desired, the sprays can be aerially applied. Soil incorporation of such surface applied herbicides is accomplished by natural leaching, and is, of course, facilitated by natural rainfall and melting snow. If desired, however, the herbicides can be incorporated into the soil by conventional tillage means.

Compounds of this invention are believed effective for emergence of postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purpose star thistle, and the like. Also controlled by the compounds of this invention are perennials such as quackgrass, Johnsongrass, Canada thistle, curley dock, field chickweed, dandelion, Russion knapweed aster, horsetail, ironweed, sesbania, cattail, wintercress, horsenettle, nutsedge, milkweed, sicklepod, and the like.

The compounds prepared as described in the Examples were individually tested for herbicidal efficacy against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was evaluated vis a vis an untreated control, by periodic visual inspection after application of the compounds. Herbicidal efficacy was evaluated on a Numerical Injury Rating (NIR) scale of from 0 (no injury) to 10 (all plants dead). A NIR rating of 7-9 indicates sever injury; a NIR rating of 4-6 indicates moderate injury, i.e., plant growth is reduced to the extent that normal growth would be expected only under ideal conditions; and a NIR rating of 1-3 indicates slight injury.

The following table gives typical preemergence and postemergence NIR data for certain of the compounds of the foregoing Examples. Each compound was applied to each weed species at a rate of 1.0 pound per acre and the NIR was determined about two weeks after application.

| Weed Species: | Compound of Example No. | | | | | | | | | |
| | I | | II | | III | | VI | | XVI | |
| | Pre | Post | Pre | Post | Pre | Post | Pre | Post | Pre | Post |
| Prickly Sida | 9 | 10 | 8 | 10 | 8 | 9 | 9 | 10 | 9 | 10 |
| Jimsonweed | 9 | 10 | 9 | 10 | 9 | 9 | 9 | 10 | 8 | 10 |
| Sicklepod | 2 | 3 | 0 | 5 | 2 | 1 | 3 | 10 | 0 | 5 |
| Lambsquarters | 10 | 10 | 10 | 10 | 10 | 10 | 10 | 10 | 10 | 8 |
| Sesbania, Hemp | 9 | 9 | 9 | 9 | 5 | 8 | 7 | 9 | 10 | 8 |
| Velvetleaf | 10 | 10 | 8 | 10 | 9 | 10 | 10 | 10 | 8 | 9 |
| Morningglory | 8 | 10 | 8 | 8 | 7 | 8 | 7 | 3 | 3 | 8 |
| Yellow Foxtail | 10 | 7 | 10 | 5 | 10 | 5 | 8 | 10 | 10 | 7 |
| Johnsongrass | 7 | 7 | 9 | 5 | 7 | 7 | 10 | 10 | 9 | 5 |
| Cultivated Oats | 5 | 3 | 5 | 0 | 5 | 2 | 2 | 3 | 2 | 1 |
| Barnyardgrass | 8 | 5 | 9 | 3 | 2 | 3 | 6 | 10 | 10 | 3 |

Although the invention has been illustrated in some detail by the foregoing, it is to be understood that many variations can be made therein by those skilled in the art without departing from the spirit and scope thereof as defined by the appended claims.

We claim:

1. A compound of the formula:

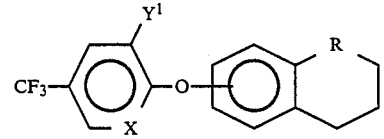

wherein:

X is N or $CY^4$ wherein $Y^4$ is hydrogen or halogen;

$Y^1$ is hydrogen or halogen and R is CO, CHOH or CNOH.

2. A herbicidal composition containing an agronomically acceptable carrier and a herbicidally effective amount of a compound or mixture of compounds defined by claim 1.

3. In a method of controlling weed growth wherein a herbicidally effective amount of herbicide is applied to the situs of the weeds wherein the improvement resides in using as the herbicide compound or mixture of compounds defined in claim 1.

* * * * *